United States Patent
Su et al.

(10) Patent No.: US 9,731,026 B2
(45) Date of Patent: Aug. 15, 2017

(54) NEAT LIQUID PHARMACEUTICAL FORMULATIONS

(71) Applicant: Massachusetts Institute of Technology, Cambridge, MA (US)

(72) Inventors: Erzheng Su, Cambridge, MA (US); Alexander M. Klibanov, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/951,055

(22) Filed: Nov. 24, 2015

(65) Prior Publication Data

US 2016/0143848 A1 May 26, 2016

Related U.S. Application Data

(60) Provisional application No. 62/084,095, filed on Nov. 25, 2014.

(51) Int. Cl.
*A61K 8/02* (2006.01)
*A61K 47/48* (2006.01)
*A61K 31/616* (2006.01)
*A61K 47/18* (2017.01)
*A61K 47/26* (2006.01)
*A61K 31/00* (2006.01)
*A61K 9/00* (2006.01)

(52) U.S. Cl.
CPC ........ *A61K 47/48092* (2013.01); *A61K 31/00* (2013.01); *A61K 31/616* (2013.01); *A61K 47/186* (2013.01); *A61K 47/26* (2013.01); *A61K 9/0019* (2013.01)

(58) Field of Classification Search
CPC ....................................................... A61K 8/02
See application file for complete search history.

(56) References Cited

U.S. PATENT DOCUMENTS

| 3,800,038 | A | 3/1974 | Rudel |
| 5,405,617 | A | 4/1995 | Gowan |
| 7,763,653 | B2 | 7/2010 | Pacheco |
| 2009/0004281 | A1* | 1/2009 | Nghiem ............... A61K 9/0004 424/490 |

OTHER PUBLICATIONS

Abbott, et al., "Novel solvent properties of choline chloride/urea mixtures", Chem. Commun., 1:70-71(2003).
Abbott, et al., "Ionic liquid analogues formed from hydrated metal salts", Chem., Eur. J., 10:3769-74 (2004).
Bica, et al., "Liquid forms of pharmaceutical co-crystals: Exploring the boundaries of salt formation", Chem Comm., 47(8):2267-9 (2011).
Grodowska, et al., "Organic solvents in the pharmaceutical industry", Acta Polomine Pharma., 67(1):3-12 (2010).
International Search Report for Corresponding PCT/US2015/062470 mailed Feb. 3, 2016.

* cited by examiner

*Primary Examiner* — Rei-Tsang Shiao
(74) *Attorney, Agent, or Firm* — Pabst Patent Group LLP

(57) ABSTRACT

Essentially non-aqueous liquid pharmaceutical formulations are formed by mixing at least one pharmaceutically active ingredient and at least one other compound capable of interacting with the active pharmaceutical ingredient through non-covalent interactions to form a low-temperature transition mixture. The stable liquid formulations are readily obtained, even with drugs that are poorly soluble and/or unstable in water.

20 Claims, 1 Drawing Sheet

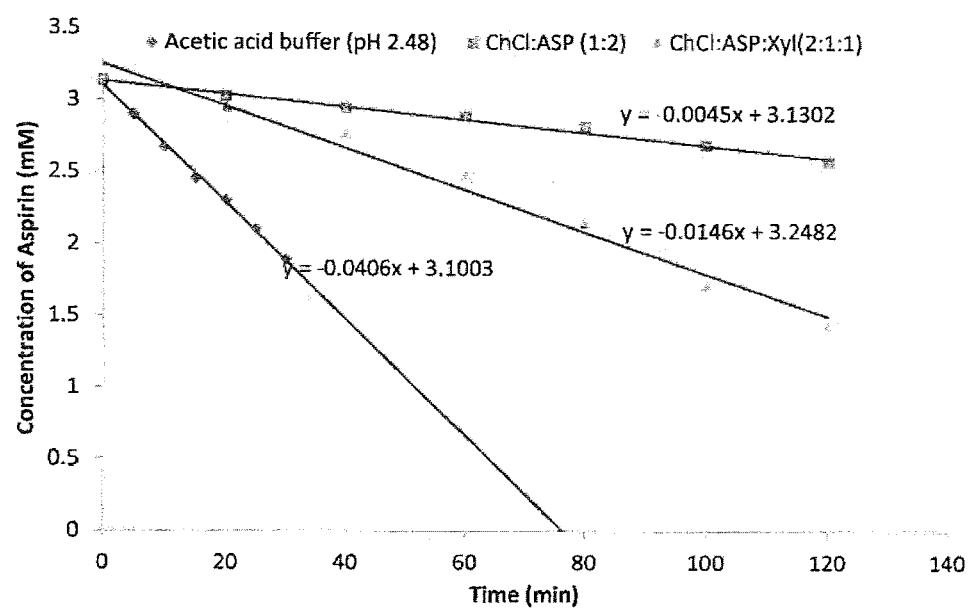

NEAT LIQUID PHARMACEUTICAL FORMULATIONS

CROSS-REFERENCE TO RELATED APPLICATIONS

This application claims benefit of and priority to U.S. Ser. No. 62/084,095 filed on Nov. 25, 2014, which is incorporated by reference in their entirety.

STATEMENT REGARDING FEDERALLY SPONSORED RESEARCH OR DEVELOPMENT

This invention was not made with government support.

FIELD OF THE INVENTION

The invention is generally directed to neat (solvent-less) liquid compositions of active pharmaceutical ingredients, including water sensitive drugs.

BACKGROUND OF THE INVENTION

Liquid formulations are commonly used to administer active pharmaceutical ingredients. Liquid formulations may be swallowed, injected, or directly applied to a variety of different tissues. Many nasal and ophthalmic products are liquid formulations. Liquid formulations for oral administration are especially useful for patients who have difficulty swallowing solid dosage forms. Because liquids can be easily divided, it is much simpler to partition a liquid formulation into smaller doses than a solid formulation.

One of the simplest types of liquid formulation is an aqueous solution. However, many active pharmaceutical ingredients ("APIs") are not sufficiently soluble in water to form practically useful solutions or those of desirable therapeutic strength. Additionally, many APIs are not stable in aqueous solution, decomposing upon long-term storage through a variety of pathways. For instance, many ester-group-containing pharmaceuticals, such as aspirin, undergo hydrolysis upon prolonged storage in water. Heterocycle-containing drugs, such as azacytidine and diazepam, undergo hydration followed by ring opening. Electrophilic drugs, such as cisplatin, can undergo nucleophilic exchange in the presence of water. Whether due to insufficient solubility, lack of stability, a combination of both, or another factor, many drugs cannot readily and conveniently, if at all, be formulated into aqueous solutions.

Although organic solvents can be used to solubilize certain drugs and minimize water-initiated decomposition, the use of organic solvents is not a practical or desirable solution in most pharmaceutical settings. Organic solvents are disfavored on regulatory grounds, due to toxicity, flammability, volatility, or environmental concerns. Furthermore, many organic solvents have an unpleasant odor or taste.

It is an object of this invention to provide liquid formulations of APIs, including poorly water-soluble or water-sensitive ones, for which the preparation of solutions or suspensions in water or organic solvents is difficult, undesirable, or impossible.

It is an object of the present invention to provide liquid formulations having a high concentration of the API(s), for example, in order to reduce the dosing size or frequency associated with the agent.

It is a further object of the invention to provide liquid formulations of APIs having enhanced stability relative to aqueous solutions of the active ingredient.

It is a still further object of the invention to provide transparent and pharmaceutically elegant liquid formulations of APIs that can be readily swallowed by a patient.

SUMMARY OF THE INVENTION

Low-temperature transition mixtures ("LTTMs") (alternatively called "deep-eutectic solvents" or "DESs") formed from at least one solid API have been developed. The LTTMs have a melting point that is lower than the melting point of the API by itself and are preferably liquid at room temperature. In addition to the API, the LTTMs contain at least one other compound capable of interacting with the API through non-covalent interactions. Because the LTTMs do not contain water or other diluents, the formulations can be substantially more concentrated than conventional aqueous or nonaqueous solutions or suspensions. Since the LTTMs do not contain essentially any water, the API may exhibit enhanced stability relative to when it is dissolved in water. The formulations may be solids, liquids, or solids which are liquified by heating.

BRIEF DESCRIPTION OF THE DRAWINGS

FIG. 1 depicts the thermal stability of two binary and ternary, respectively, LTTMs (choline chloride:aspirin (1:2) [square data points] and choline chloride:aspirin:xylitol (2:1:1) [triangle data points]) compared to a conventional aqueous formulation (aspirin dissolved in acetic acid aqueous buffer, pH 2.5 [circle data points]).

DETAILED DESCRIPTION OF THE INVENTION

I. Definitions

As used herein, the term "active pharmaceutical ingredient" (or "API") refers to a chemical compound (or mixture of compounds) that causes a change in a biological substrate. Exemplary classes of APIs in the medical and biological arts include therapeutic, prophylactic, and diagnostic agents. The API may be a small-molecule or macromolecular drug.

As used herein, the terms "deep-eutectic solvent" ("DES") and "low-transition-temperature mixture" ("LTTM") are used interchangeably to describe liquid compositions having at least two components which interact with each other via non-covalent bonds to form a low-transition-temperature mixture (or deep-eutectic solvent), typically transparent and preferably liquid at room temperature, which exhibits a substantially lower melting point than the isolated individual components. An eutectic system describes a homogeneous mix of chemical species, to form a joint super-lattice, by striking a unique atomic or molecular percentage ratio between the components—as each pure component has its own distinct bulk lattice arrangement. It is only in this atomic or molecular ratio that the eutectic system melts as a whole, at a specific temperature (the eutectic temperature), the super-lattice releasing at once all its components into a liquid mixture. The eutectic temperature is the lowest possible melting temperature over all of the mixing ratios for the involved component species. Upon heating any other mixture ratio and reaching the eutectic temperature, one component's lattice will melt first, while the temperature of the mixture has to further increase for the other component's lattice to melt. Conversely, as a non-eutectic mixture cools down, each mixture's component will solidify (form its lattice) at a distinct temperature, until all material is solid. The coordinates defining a eutectic point are the eutectic percentage ratio (on the molecular ratio or horizontal axis) and the eutectic temperature (on the temperature or vertical axis).

As used herein, the term "non-covalent interactions" refers to electrostatic bonds, including ionic bonds, dipole-dipole interactions, of which hydrogen bonds are a subset, Van der Waals interactions, and/or London forces.

As used herein, "dipole-dipole interactions" refer to attractions between an electropositive and electronegative atoms or groups of atoms. "Electropositive" and "electronegative" describe atoms having lower, or greater electron density, respectively, surrounding the nucleus relative to the atom in the elemental state.

The term "essentially water-free" describes a liquid composition that contains less than 5%, less than 4%, less than 3%, less than 2%, less than 1%, less than 0.5%, less than 0.1%, and 0% weight by weight water, as measured using the Karl Fischer titration method.

The term "hydrogen bond" refers to electrostatic interactions between an electropositive hydrogen atom and an electronegative atom. Electropositive hydrogen atoms occur when a hydrogen atom is covalently bonded to an electronegative atom, such as oxygen or nitrogen. Exemplary functional groups having electropositive hydrogen atoms include hydroxyl, oxime, thiol, carboxylic acid, sulfonic acid, phosphoric acid, primary and secondary amides, primary and secondary amines, and imines.

Exemplary electronegative atoms capable of interacting with an electropositive hydrogen via hydrogen-bonding include oxygen, nitrogen, and fluorine.

As used herein, the term "hydrogen bond acceptor" refers to a compound having at least one electronegative atom (such as oxygen, nitrogen, and fluorine) capable of interacting with an electropositive hydrogen atom through a hydrogen bond.

As used herein, the term "hydrogen bond donor" refers to a compound having at least one electropositive hydrogen atom capable of interacting with an electronegative atom through a hydrogen bond.

As used herein, the term "primary amine" refers to the functional group $RNH_2$, wherein R is a non-hydrogen group of atoms, such as alkyl or aryl. As used herein, the term "secondary amine" refers to the functional group RR'NH, wherein R and R' are both non-hydrogen groups of atoms, such as alkyl or aryl. Secondary amines include heterocyclic structures such as pyrrolidine and imidazole. The term "tertiary amine" refers to the functional group RR'R"N, wherein R, R', and R" non-hydrogen atom non-hydrogen groups of atoms, such as alkyl or aryl. Tertiary amines include heterocyclic structures such as pyridine.

As used herein, the term "primary amide" refers to the functional group $RC(=O)NH_2$, wherein R is a non-hydrogen group of atoms, such as alkyl or aryl.

As used herein, the term "secondary amine" refers to the functional group $RC(=O)NHR'$, wherein R and R' are non-hydrogen group of atoms, such as alkyl or aryl. Secondary amides include heterocyclic structures such as thymine and guanine.

As used herein, the term "pharmaceutically acceptable salts" refers to salts prepared from pharmaceutically acceptable acids and bases, including inorganic and organic acids and bases. Suitable pharmaceutically acceptable acids include inorganic and organic acids, such as acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, tetrafluoroboric, pamoic, pantothenic, phosphoric, succinic, sulfuric, tartaric, p-toluenesulfonic, and the like. Suitable pharmaceutically acceptable bases include inorganic and organic bases, such as sodium hydroxide, potassium hydroxide, lithium hydroxide, calcium hydroxide, magnesium hydroxide, ammonium hydroxide, and amines.

II. Deep Eutectic Solvents/Low Temperature Transition Mixtures

A. Solvents and LTTM

LTTMs, or DESs, are formed from the combination of two or more compounds which, when separate, have melting points higher than when the components are combined. For instance, a deep-eutectic solvent is produced by combining urea (mp=133° C.) with choline chloride (mp=302° C.) in a 2:1 molar ratio. The resulting liquid has a melting point of 12° C. *Chem. Commun.* (2003) 70-71; *Chem., Eur. J.* (2004) 10:3769-3774. As DESs can be made from environmentally benign constituents, they have been explored as alternatives to traditional solvents for chemical transformations.

The LTTMs disclosed herein contain at least two compounds capable of associating with each other through non-covalent interactions. In preferred embodiments, the non-covalent interactions include hydrogen bonds between the two compounds. In certain embodiments, the LTTM is a binary mixture, and in other embodiments it is a ternary mixture. Higher order mixtures may also be formed. One or more of the compounds in the mixture is a pharmaceutically active agent, so long as it is also a hydrogen bond acceptor and/or hydrogen bond donor. Such LTTMs may also include other agents, such as sweeteners and other taste-masking compounds, flavors, fragrances, colorants, and others.

For LTTMs that contain compounds that interact via hydrogen bonds, one of the compounds must contain at least one hydrogen bond accepting functional group and the other compound must contain at least one hydrogen bond donating functional group. One or more of the compounds in the mixture may contain both hydrogen bond donating and hydrogen bond accepting groups. In some embodiments, one or more of the compounds in the mixture is taken from the list of compounds identified by the FDA as Generally Recognized as Safe ("GRAS") or contained in the FDA Inactive-ingredient Guide ("IIG").

One of the compounds in the LTTM may contain at least one carboxylic group. Exemplary carboxylic group containing compounds include oxalic acid, malonic acid, lactic acid, maleic acid, fumaric acid, malic acid, tartaric acid, citric acid, itaconic acid, benzoic acid, 4-hydroxybenzoic acid, cinnamic acid, caffeic acid, gallic acid, phenylacetic acid, succinic acid, coumaric acid, adipic acid, sebacic acid, decanoic acid, stearic acid, oleic acid, linoleic acid, propionic acid, and acetic acid.

One of the compounds in the LTTM may contain at least one hydroxyl group. Exemplary compounds having at least one hydroxyl group include ethanol, isopropanol, t-butanol, butanol, isobutanol, α-isosorbide, glycerol, propylene glycol, and resorcinol.

One of the compounds in the LTTM may be a sugar. Exemplary sugars include glucose, sorbose, ribose, mannose, sucrose, lactose, fructose, fucose, rhamnose, lyxose, ribose, arabinose, allose, altrose, gulose, idose, talose, galactose, and xylose.

One of the compounds in the LTTM may be a sugar alcohol. Exemplary sugar alcohols include glucitol, sorbitol, ribotol, mannitol, fucitol, ribitol, rhamnitol, arabitol, idotol, galactitol, and xylitol.

One of the compounds in the LTTM may be an amino acid. Exemplary amino acids include L-enantiomers of histidine, isoleucine, leucine, lysine, methionine, phenylalanine, threonine, tryptophan, valine, alanine, arginine, asparagine, aspartic acid, cysteine, glutamic acid, glutamine, glycine, ornithine, proline, selenocysteine, serine, and tyrosine.

One of the compounds in the LTTM may contain at least one amide, carbamate, or carbamide group. Exemplary compounds include acetamide, urea, 1,1-dimethylurea, 1,3-dimethylurea, nicotinamide, tetramethylurea, propylene urea, 1-methylurea, 2-imidazolidinone, and benzamide.

One of the compounds in the LTTM may contain at least one amino group. Exemplary compounds include imidazole, ethylamine, trimethylamine, alanine, glycine, proline, nicotinic acid, histidine, (2-hydroxyethyl)-diethylamine, articaine, tetracaine, proxymetacaine, metoclopramide, procaine, lidocaine, cyclomethylcaine, piperocaine, chloroprocaine, etidocaine, benzocaine, phenylephrine, bupivacaine, mepivacaine, cinchocaine, and pharmaceutically acceptable salts thereof. In embodiments in which the LTTMs contain lidocaine, the mixture preferably does not contain a carboxylic group containing compound, and more preferably does not contain acrylic acid or methacrylic acid.

In certain embodiments, the LTTMs contain a quaternary ammonium salt. Exemplary quaternary ammonium compounds include pharmaceutically acceptable salts of tetraalkyl ammonium compounds, such as tetramethylammonium, tetraethylammonium, betaine, choline, 2-chlorocholine, 2-fluorocholine, acetylcholine, and derivatives thereof. Phosphonium salts can be used as hydrogen bond acceptors.

In certain embodiments, the low-temperature transition mixtures may be depicted by the formula:

$$A_x:B_y:C_z$$

wherein A represents the API, B and C (when C is present) represent compounds capable of interacting with one of the other compounds in the mixture through non-covalent bonds, and x, y and z are independently selected from any number from 0.25 to 5.

In certain embodiments, z is 0, B is a quaternary ammonium salt, and x is 1. In other preferred embodiments, B is a quaternary ammonium salt, x is 1, and C is an amino acid, sugar, reduced sugar, or carboxylic group-containing compound.

In other preferred embodiments, z is 0, A is aspirin or acetaminophen, and B is a pharmaceutically acceptable salt of choline, such as choline chloride. In other preferred embodiments, A is aspirin, B is a quaternary ammonium salt, and C is a reduced sugar.

In certain embodiments, A is not lidocaine.

The LTTMs are characterized by a melting point that is lower than that of the API. In some embodiments, the LTTM may have a melting point that is less than about 100°, 75°, 50°, 40°, 35°, 30°, 25°, 20°, 15°, 10°, 5°, 0°, −5°, −10°, −15° or −20° C. In some embodiments, the LTTM looks transparent to a naked eye.

The LTTMs form liquids having viscosities suitable for use in pharmaceutical and other biomedical applications. The liquids may have a viscosity less than about 10,000, 7,500, 5000, 2,500, 1,000, 750, 500, 250, 150, 100, 75, 50, 25, 20, 15, 10, or 5 cps, when measured at 25° C. using a device such as a calibrated dropper.

B. Pharmaceutically Acceptable Agents

APIs include pharmaceutically acceptable therapeutic, prophylactic, and/or diagnostic agents. They can be both prescription and over-the-counter medications.

Water sensitive APIs may exhibit increased stability when formulated as LTTMs relative to when they are dissolved in aqueous solution. For example, the half-life of the agent in a LTTM is often twice, five times, ten times, twenty times or even fifty times or more, greater than that of the API dissolved in water.

Exemplary APIs for use in LTTMs include non-steroidal anti-inflammatory drugs, such as aspirin, acetaminophen, diflunisal, ibuprofen, naproxen, dexibuprofen, fenoprofen, dexketoprofen, flurbiprofen, oxaprozin, loxoprofen, ketoprofen, diclofenac, sulindac, tolmetin, indomethacin, etodolac, ketorolac, aceclofenac, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, firoxocib, nimesulide, clonixin, licofelone, and pharmaceutically acceptable salts thereof.

The API may be an HMG-CoA reductase inhibitor, such as atorvastatin, cerivastatin, fluvastatin, lovastatin, mevastatin, pitavastatin, pravastatin, rosuvastatin, simvastatatin, and pharmaceutically acceptable salts thereof.

The API may be an opioid-derived analgesic, such as morphine, codeine, diacetylmorphine, buprenorphine, etorphine, hydrocodone, hydromorphone, oxycodone, oxymorphone, and pharmaceutically acceptable salts thereof.

The active API may be an antidepressant or antipsychotic, such as citalopram, escitalopram, paroxetine, fluoxetine, fluvoxamine, sertraline, zimelidine, indalpine, desvenlafaxine, duloxetine, levomilnacipran, milnacipran, tofenacin, venlafaxine, vilazodone, vortioxetine, etoperidone, trazodone, nefazodone, reboxetine, viloxazine, atomoxetine, amitriptyline, amitriptylinoxide, clomipramine, desipramine, dibenzepin, dosulepin, doxepin, imipramine, lofepramine, melitracen, nitroxazepine, nortriptyline, noxiptiline, pipofezine, protriptyline, trimipramine, butriptyline, demexiptiline, imipraminoxide, iprindole, metapramine, propizepine, quinupramine, opipramol, tianeptine, amineptine, tiazesim, amoxapine, maprotiline, mianserin, mirtazapine, setiptiline, mianserin, mirtazapine, setiptiline, isocarboxazid, phenelzine, tranylcypromine, benmoxin, iproclozideiproniazid, mebanazine, nialamide, octamoxin, pheniprazine, phenoxypropazine, pivhydrazine, safrazine, selegiline, caroxazone, metralindole, moclobemide, pirlindole, toloxatone, eprobemide, minaprine, agomelatine, amisulpride, buprenorphine, bupropion, ketamine, lurasidone, tandospirone, teniloxazine, etryptamine, medifoxamine, metryptamine, nomifensine, oxaflozane, ademetionine, oxitriptan, tryptophan, aripiprazole, lurasidone, olanzapine, quetiapine, risperidone, ziprasidone, buspirone, lithium, thyroxine, triiodothyronine, and pharmaceutically acceptable salts thereof.

The API may be an antihistamine, such as acrivastine, azelastine, emadastine, epinastine, brompheniramine, carbinoxamine, cetirizine, chlorpheniramine, clamastine, cyproheptadine, desloratidine, diphenhydramine, naphazoline, fexofenadine, hydroxyzine, ketotifen, levociterizine, loratadine, olopatadine, and pharmaceutically acceptable salts thereof. Montelukast, ipratropium and pharmaceutically acceptable salts thereof may also be employed.

The API may be mast cell stabilizer, such as cromolyn, lodoxamine, nedocromil, pemirolast, and pharmaceutically acceptable salts thereof.

The API may be a corticosteroid such as cortisone, dexamethasone, fluticasonse propionate, fluticasone furoate, beclomethasone diproprionate, budesonide, ciclesonide, flunisolide, hydrocortisone, loteprednol, mometasone furoate, methylprednisolone, prednisolone, prednisone, triamcinolone acetate, and pharmaceutically acceptable salts thereof.

The API may be a proton pump inhibitor, such as omeprazole, lansoprazole, dexlansoprazole, esomeprazole, pantoprazole, rabeprazole, illaprazole, and pharmaceutically acceptable salts thereof. The API may also be a $H_2$-receptor antagonist, such as cimetidine, ranitidine, and pharmaceutically acceptable salts thereof.

The formulation may be a solid, liquid or solid which can be converted to liquid by heating. Liquids may be injectable or suspendable or dissolvable to form a dispersion or solution for oral ingestion, in liquid form or in a soft or hard gel capsule. Sweeteners, other taste masking agents, flavors, colorants. In general, pharmaceutical compositions are provided including effective amounts of the active agent(s) and optionally include pharmaceutically acceptable diluents, preservatives, solubilizers, emulsifiers, adjuvants and/or carriers. Such compositions can include anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles including propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

III. Methods of Making Low-Temperature-Transition Mixtures

The LTTMs may be prepared by combining the individual components, heating the mixture to a temperature sufficient to melt and form the LTTM, and the allowing the mixture to cool to room temperature. Temperatures from about 30° C. to about 100° C. are generally sufficient to generate the LTTM. Preferably the temperature is from about 60° C. to about 100° C.

The LTTM may then be stored at temperatures from about −20° C. to about 37° C.

IV. Methods of Using Low-Temperature-Transition Mixtures

The LTTMs may be administered orally, by injection, and topically. For oral administration, the mixtures optionally may be encapsulated in a suitable shell, such as those made from gelatin. Because the LTTMs do not require a separate solvent, the physical size of the dosage form is often much smaller than of conventional liquid formulations. Other excipients include sweeteners, other taste masking agents, flavorings, and diluents.

The LTTMs may be administered via injection using conventional techniques. Since additional solvent is not required to form the liquid, the volume of fluid administered is typically much less than used in conventional formulations.

For topical administration, the low-temperature transition mixtures may be directly applied to the skin, mucosa, eye, ear, or other relevant tissue, including such modes of administration as nasal, ocular, buccal, sublingual, anal, vaginal, and transdermal. Since the viscosity of the mixture may be adjusted by selection of the appropriate components and compound ratios, the mixture may be designed to adhere closely to the targeted tissue. By direct application of a highly viscous liquid containing the API, a more concentrated dose of drug may be administered to the tissue than is possible with conventional solution and suspension formulations. Such applications may find use for the local administration of APIs to tumors and other discreet tissue targets. Conversely, application of a low viscosity liquid to tissue will result in rapid disbursement of the drug over the entire surface of the tissue. Such applications may find use in the application of drugs to surfaces such as those found on the eye.

The present invention will be further understood by reference to the following non-limiting examples.

EXAMPLES

Example 1

Preparation of Low-Temperature Transition Mixtures

The following aspirin-containing low temperature transition mixtures were prepared by combining the individual solids in the listed ratios, mixing thoroughly, heating to 60-100° C., and cooling to room temperature. The results are shown in Table 1.

TABLE 1

Summary of studies to prepare aspirin-containing LTTMs

| | | | | | |
|---|---|---|---|---|---|
| 1 | Choline chloride | Aspirin | None | 1:1 | Extremely viscous liquid |
| 2 | Choline chloride | Aspirin | None | 1:2 | Viscous liquid |
| 3 | Choline chloride | Aspirin | None | 1:3 | Viscous liquid |
| 4 | Choline chloride | Aspirin | None | 2:1 | Unable to form a liquid |
| 5 | Choline bitartrate | Aspirin | None | 1:2 | Unable to form a liquid |
| 6 | Betaine | Aspirin | None | 1:2 | Viscous liquid |
| 7 | L-histidine | Aspirin | None | 1:2 | Unable to form a liquid |
| 8 | Glycine | Aspirin | None | 1:2 | Unable to form a liquid |
| 9 | L-proline | Aspirin | None | 1:2 | Unable to form a liquid |
| 10 | L-glutamic | Aspirin | None | 1:2 | Unable to form a liquid |

TABLE 1-continued

Summary of studies to prepare aspirin-containing LTTMs

| | | | | | |
|---|---|---|---|---|---|
| | acid | | | | |
| 11 | D-glucose | Aspirin | None | 1:1 | Unable to form a liquid |
| 12 | Choline chloride | Aspirin | L-proline | 1:1:1 | Viscous liquid |
| 13 | Betaine | Aspirin | L-proline | 1:1:1 | Viscous liquid |
| 14 | Choline chloride | Aspirin | D-glucose | 1:1:1 | Unable to form a liquid |
| 15a | Choline chloride | Aspirin | Tartaric acid | 1:1:1 | Unable to form a liquid |
| 15b | Choline chloride | Aspirin | Tartaric acid | 3:1:1 | Viscous liquid |
| 16a | Choline chloride | Aspirin | L-malic acid | 1:1:1 | Unable to form a liquid |
| 16b | Choline chloride | Aspirin | L-malic acid | 2:1:1 | Viscous liquid |
| 17a | Choline chloride | Aspirin | Citric acid | 1:1:1 | Viscous liquid |
| 17b | Choline chloride | Aspirin | Citric acid | 2:1:1 | Unable to form a liquid |
| 18a | Choline chloride | Aspirin | Urea | 1:1:1 | Unable to form a liquid |
| 18b | Choline chloride | Aspirin | Urea | 2:1:1 | Viscous liquid |
| 19a | Choline chloride | Aspirin | Glycine | 1:1:1 | Unable to form a liquid |
| 19b | Choline chloride | Aspirin | Glycine | 2:1:1 | Unable to form a liquid |
| 20 | Choline chloride | Aspirin | D-xylitol | 1:1:1 | Liquid |
| 21 | Choline chloride | Aspirin | D-xylitol | 2:1:0.5 | Unable to form a liquid |
| 22 | Choline chloride | Aspirin | D-xylitol | 2:1:0.65 | Initially a liquid, solidified after 48 hours |
| 23 | Choline chloride | Aspirin | D-xylitol | 2:1:0.75 | Initially a liquid, solidified after 5 days |
| 24 | Choline chloride | Aspirin | D-xylitol | 2:1:1 | Liquid |
| 25 | Choline chloride | Aspirin | D-xylitol | 2:1:1.5 | Initially a liquid, solidified after 5 days |
| 26 | Choline chloride | Aspirin | D-xylitol | 2:1:1.75 | Initially a liquid, solidified after 4 days |
| 27 | Choline chloride | Aspirin | D-xylitol | 2:1:2 | Initially a liquid, solidified after 5 hours |
| 28 | Choline chloride | Aspirin | D-xylitol | 2:1:3 | Initial liquid, solidified after 24 hours |
| 29 | Choline chloride | Aspirin | D-xylitol | 2:1:4 | Initially a liquid, solidified after 24 hours |
| 30 | Choline chloride | Aspirin | D-xylitol | 2:1:5 | Initially a liquid, solidified after 24 hours |
| 31 | Choline chloride | Aspirin | D-xylitol | 3:1:1 | Unable to form a liquid |
| 32 | Choline chloride | Aspirin | D-mannitol | 2:1:0.25 | Unable to form a liquid |
| 33 | Choline chloride | Aspirin | D-mannitol | 2:1:0.5 | Unable to form a liquid |
| 34 | Choline chloride | Aspirin | D-mannitol | 2:1:0.75 | Initially a liquid, solidified after 5 days |
| 35 | Choline chloride | Aspirin | D-mannitol | 2:1:1 | Initially a liquid, crystallized after 11 days |
| 36 | Choline chloride | Aspirin | D-mannitol | 2:1:1.25 | Unable to form a liquid |
| 37 | Choline chloride | Aspirin | D-mannitol | 2:1:1.5 | Initially a liquid, solidified after 5 days |
| 38 | Choline chloride | Aspirin | D-mannitol | 2:1:1.75 | Initially a liquid, solidified after 5 days |
| 39 | Choline chloride | Aspirin | D-mannitol | 2:1:2 | Initially a liquid, solidified after 24 hours |
| 40 | Choline chloride | Aspirin | D-mannitol | 2:1:3 | Unable to form a liquid |
| 41 | Choline chloride | Aspirin | D-sorbitol | 2:1:0.5 | Unable to form a liquid |
| 42 | Choline chloride | Aspirin | D-sorbitol | 2:1:0.65 | Initially a liquid, solidified after 3 days |
| 43 | Choline chloride | Aspirin | D-sorbitol | 2:1:0.75 | Initially a liquid, solidified after 5 days |
| 44 | Choline chloride | Aspirin | D-sorbitol | 2:1:1 | Initially a liquid, solidified after 12 days |
| 45 | Choline | Aspirin | D-sorbitol | 2:1:1.25 | Viscous liquid, began to |

TABLE 1-continued

Summary of studies to prepare aspirin-containing LTTMs

| | | | | | |
|---|---|---|---|---|---|
| | chloride | | | | crystallize after 3 days |
| 46 | Choline chloride | Aspirin | D-sorbitol | 2:1:1.5 | Initially a liquid, solidified after 2 days |
| 47 | Choline chloride | Aspirin | D-sorbitol | 2:1:2 | Initially a liquid, solidified after 10 days |
| 48 | Choline chloride | Aspirin | D-sorbitol | 2:1:2.25 | Initially a liquid, solidified after 3 hours |
| 49 | Choline chloride | Aspirin | D-sorbitol | 2:1:2.5 | Initially a liquid, solidified after 18 hours |
| 50 | Choline chloride | Aspirin | D-sorbitol | 2:1:3 | Initially a liquid, solidified after 4 days |

Similar results as in the table above were obtained with acetaminophen instead of aspirin.

Example 2

Aspirin Thermal Stability Measurements in LTTMs

Owing to its relatively unstable ester bond, aspirin can undergo degradation to form salicylic and acetic acids. Low temperature transition mixtures #2 and 24 from Example 1 were subjected to further investigation with respect to aspirin's stability. Toward this end, the following procedures were carried out:
1) Pretreated 3-Å molecular sieve beads were added to each LTTM in a vial. Then the vials containing the LTTMs were placed in a desiccator under vacuum at room temperature for 24 h.
2) Transfer 3 mL of the dehydrated LTTM to a clean vial containing a stirr bar.
3) Glycerol bath was heated to 95° C.
4) The vial was immersed in the glycerol bath, and the LTTM was stirred at 300 rpm until the temperature of the LTTM reached 95° C.
5) The LTTM samples were diluted to an appropriate volume, and their absorbance at 300 nm (the maximum absorption wavelength of salicylic acid) was measured using a UV/V is spectrophotometer. The concentration of salicylic acid in the LTTM was calculated using a previously obtained standard curve, and then the residual concentration of aspirin was calculated using the mass balance.

The results obtained are shown in Table 2, and FIG. 1 depicts the disappearance of aspirin over time when the LTTM mixtures and aqueous solution were heated to 95° C. The decomposition half-lives of the formulations are presented below.

TABLE 2

Stability of aspirin over time when the LTTM mixtures and aqueous solution were heated to 95° C.

| Formulation | Half-life (min) |
|---|---|
| Aspirin in acetic acid buffer (pH 2.5) | 41.2 |
| Choline chloride:aspirin (1:2) | 418 |
| Choline chloride:aspirin:xylitol (2:1:1) | 106 |

We claim:

1. An essentially water-free, low-transition-temperature mixture (LTTM) comprising at least one pharmaceutically active agent selected from the group consisting of a non-steroidal anti-inflammatory drug, a HMG-CoA reductase inhibitor, an analgesic, an antidepressant, an antipsychotic, an antihistamine, a mast cell stabilizer, a corticosteroid, a proton pump inhibitor, and combinations thereof, non-covalently bound to at least one pharmaceutically acceptable excipient,
wherein the LTTM conforms to the stoichiometric formula:

$A_x:B_y:C_z$ wherein A represents the pharmaceutically active agent; B and, optionally C, are pharmaceutically acceptable excipients capable of interacting with one of the other compounds in the LTTM, including A, through non-covalent bonds; and x, y, and z are independently selected from any number between about 0.25 to about 5,
wherein the active agent is a hydrogen-bond donor or a hydrogen bond acceptor,
wherein the LTTM comprises a hydrogen-bond donor and a hydrogen bond acceptor, and
wherein the melting point of the LTTM is lower than the melting point of the pharmaceutically acceptable excipient(s), and the active agent alone.

2. The LTTM of claim 1, wherein the melting point of the mixture is less than about 50°, 40°, 35°, 30°, 25°, 20°, 15°, 10°, 5°, 0°, −5°, −10°, −15° or −20° C.

3. The LTTM of claim 1 which is pharmaceutically acceptable for enteral administration and looks transparent to a naked eye.

4. The LTTM of claim 1, wherein B and C are independently selected from the group consisting of a quaternary ammonium salt, a phosphonium salt, an amino-containing compound, an amide-containing compound, a carboxylic acid-containing compound, and a hydroxyl-containing compound.

5. The LTTM of claim 1, wherein B is a quaternary ammonium salt and x is about 1.

6. The LTTM of claim 1, wherein B is a quaternary ammonium salt, x is about 1, and C is selected from the group consisting of an amino acid, a sugar, a sugar alcohol, and a carboxylic group-containing compound.

7. The LTTM of claim 1 wherein the therapeutic agent is selected from the group consisting of aspirin, famotidine, cetirizine, acetaminophen, and ibuprofen.

8. The LTTM of claim 1, wherein B is a pharmaceutically acceptable salt of choline.

9. The LTTM of claim 8, wherein the pharmaceutically acceptable salt of choline is choline chloride.

10. The LTTM of claim 1, wherein A is aspirin or acetaminophen, B is a quaternary ammonium salt, and C is a sugar alcohol.

11. The LTTM of claim 10, wherein the sugar alcohol is selected from the group consisting of xylitol, glucitol, sorbitol, ribotol, mannitol, fucitol, ribitol, rhamnitol, arabitol, idotol, and galactitol.

12. The LTTM of claim 1 in a dosage formulation for administration to an individual in need thereof.

13. The LTTM of claim 12 wherein the dosage formulation is for administration topically or by inhalation to a mucosal surface.

14. The LTTM of claim 12 wherein the dosage formulation is in a liquid form at room temperature.

15. The LTTM of claim 12 wherein the dosage formulation further comprises one or more excipients selected from the group consisting of taste masking agents, stabilizers, antioxidants, colorants, preservatives, and flavorings.

16. A method of making the LTTM of claim 1, comprising the steps of:
   a) combining A, B, and, optionally, C in their solid state;
   b) heating the mixture to a temperature sufficient to melt the solids; and
   c) cooling the mixture to ambient temperature to retain a liquid.

17. The method of claim 16 wherein ambient temperature is between about 18 and 24° C.

18. A method of delivering at least one active pharmaceutical compound comprising the step of administering the LTTM of claim 1 to an individual in need thereof.

19. The method of claim 18 wherein the LTTM is administered orally, nasally, ocularly, or transdermally.

20. The method of claim 18 wherein the LTTM is administered by injection.

* * * * *